(12) United States Patent
Edwards (10) Patent No.: US 9,898,156 B2
(45) Date of Patent: Feb. 20, 2018

(54) METHOD AND COMPUTING DEVICE FOR WINDOW WIDTH AND WINDOW LEVEL ADJUSTMENT UTILIZING A MULTITOUCH USER INTERFACE

(71) Applicant: Change Healthcare LLC, Alpharetta, GA (US)

(72) Inventor: Cliff Edwards, Delta (CA)

(73) Assignee: CHANGE HEALTHCARE LLC, Alpharetta, GA (US)

( * ) Notice: Subject to any disclaimer, the term of this patent is extended or adjusted under 35 U.S.C. 154(b) by 229 days.

(21) Appl. No.: 14/447,083

(22) Filed: Jul. 30, 2014

(65) Prior Publication Data

US 2016/0034110 A1    Feb. 4, 2016

(51) Int. Cl.
G06F 3/0488    (2013.01)
G06F 3/0481    (2013.01)
G06F 3/0484    (2013.01)
G06F 19/00    (2018.01)

(52) U.S. Cl.
CPC ........ *G06F 3/0481* (2013.01); *G06F 3/04845* (2013.01); *G06F 3/04847* (2013.01); *G06F 3/04883* (2013.01); *G06F 19/321* (2013.01); *G06F 2203/04808* (2013.01)

(58) Field of Classification Search
CPC ........ G06F 3/04883; G06F 3/017; G06F 3/04; G06F 3/04886; G06T 2207/00
See application file for complete search history.

(56) References Cited

U.S. PATENT DOCUMENTS

| | | | |
|---|---|---|---|
| 8,334,867 B1 * | 12/2012 | Davidson | G06F 3/04815 345/419 |
| 9,324,188 B1 * | 4/2016 | Fram | G06T 19/00 |
| 2009/0138800 A1 * | 5/2009 | Anderson | G06F 3/04883 715/702 |
| 2014/0022194 A1 * | 1/2014 | Ito | G06F 3/0488 345/173 |
| 2014/0118281 A1 * | 5/2014 | Baker | G06F 3/0418 345/173 |

OTHER PUBLICATIONS

Idea Map Board on Digital Signage—Sotouch http://www.sotouch-tech.com/2014DSE.html (published by Sotouch Technology Co. on Feb. 11, 2014).*
Brightness / Contrast Adjustment [online] [retrieved Aug. 29, 2014]. Retrieved from the Internet: <URL: http://cpboyd.wordpress.com/2013/12/14/brightness-contrast-adjustment/. (Dated Dec. 14, 2013); 3 pages.

* cited by examiner

*Primary Examiner* — Rinna Yi
(74) *Attorney, Agent, or Firm* — Alston & Bird LLP (57) ABSTRACT

A method, computing device and computer program product are provided in order to utilize a multitouch user interface so as to adjust the window width and window level of an image. In the context of a method, an indication of user input provided via a multitouch user interface is received. The indication of user input includes an indication of respective positions of first and second fingers upon the multitouch user interface. The method also includes adjusting, with processing circuitry, a window width of an image based upon a change in spacing between the first and second fingers. Further, the method includes adjusting, with the processing circuitry, a window level of the image based upon a change in location of a reference point defined by the respective positions of the first and second fingers upon the multitouch user interface.

16 Claims, 7 Drawing Sheets

METHOD AND COMPUTING DEVICE FOR WINDOW WIDTH AND WINDOW LEVEL ADJUSTMENT UTILIZING A MULTITOUCH USER INTERFACE

TECHNOLOGICAL FIELD

An example embodiment of the present invention relates generally to window width and window level adjustment and, more particularly, to a method, computing device and computer program product for utilizing a multitouch user interface to provide for window width and window level adjustment.

BACKGROUND

Medical images are captured by a wide variety of modalities including, for example, computerized tomography (CT), magnetic resonance imaging (MRI), computed radiography (CR), digital radiography (DR), and mammography (MG). Regardless of the modality, the medical images are comprised of a plurality of pixels, each of which has a respective pixel value. Once visualized, each pixel value corresponds to a distinct gray level or a distinct shade of color, such as red, green or blue depending upon the respective color channel. Many modalities, such as each of the foregoing examples, have pixels with a relatively large range of values, thereby defining a dynamic pixel value range. In this regard, the range of pixel values may be substantially greater than the 256 display values that most displays are capable of presenting. For example, depending upon whether the image is an original image or has been post-processed, the pixel range of an image could be expressed by 10 bits so as to have 1024 different pixel values, 12 bits so as to have 4096 different pixel values or 16 bits so as to have 65536 different pixel values.

Most displays and most operating systems that support the display of medical images only allow for 256 shades of gray (in an instance in which a grey scale monitor is utilized) or 256 shades of each of red, green and blue colors (in an instance in which a color monitor having red, green and blue color channels is utilized) to be simultaneously displayed. Due to the differences between the dynamic pixel value range and the number of different display values that may be simultaneously presented by a display, the dynamic pixel value range may be divided into intervals, each of which has an equal number of different values, e.g., 256 different pixel values, as those which can be simultaneously presented by display. Within the interval of pixel values, the different pixel values are represented by different shades of gray or different shades of color. For pixel values that are below the minimum pixel value of the interval, the pixel values may be mapped to the minimum display value of the interval. Similarly, for pixel values that are above the maximum pixel value of the interval, the pixel values may be mapped to the maximum display value of the interval.

A user may modify the interval across the full dynamic pixel value range so as to permit the user to view the other pixel values. The interval may be defined in terms of a window and a level. The width of the interval in terms of the range of pixel values is termed the window with the center of the range of pixel values within the window being termed the level. In general, a window may be of any size with the windowing process mapping the pixel value range of the window from [center−width/2, center+width/2] to the nearest integer [0-255] for a display capable of presenting 256 shades. The mapping of the pixel values to the display intensities may be performed in accordance with a function. Depending on the type of function, a group of pixels may map to some grayscale (or color) values or some grayscale (or color) values may not be used at all.

This mapping of pixel values and output intensities is generally termed window leveling. In many modalities, the optimal window level is not known in advance and users must manually modify the window level until a proper value is found. This modification of the window level may be performed by user interaction with an image viewer application, such as a Picture Archiving and Communication System (PACS) viewer, through an input device, such as a mouse. In this regard, a user may modify the window level by moving the window throughout the dynamic pixel value range so as to permit different pixel values to be displayed. In an instance in which the dynamic pixel value range exceeds the number of different pixel values that may be simultaneously presented by a display, some of the pixel values of the input image will not be accurately represented by the image presented by the display regardless of the window leveling. Indeed, pixel values of the input images that fall outside the window may be represented or rather, mis-represented, by a pixel value within the window. A user viewing the image presented by the display may not recognize the modification of the pixel values and, as a result, may not realize that the visual representation of the input image does not entirely accurately reflect the input image.

In order to utilize a mouse to control the window width and window level of an image, movement of the mouse in a first direction is generally associated with the adjustment of the window width, while the movement of the mouse in a second direction, such as perpendicular to the first direction, permits adjustment of the window level. Movement of the mouse in a direction that includes components of both the first and second directions, such as movement in a diagonal direction, may permit the window width and level to both be simultaneously adjusted with the extent of the adjustment of the window width and the window level depending upon the movement of the mouse in the respective directions.

While generally effective, the use of a mouse to adjust the window width and window level of an image is not necessarily intuitive and is not necessarily the most efficient and effective input technique. In this regard, a user must remember the different directions in which the mouse must be translated in order to separately adjust the window width and window level. While the movement of the mouse in a direction that includes components in both the first and second directions associated with adjustment of the window width and the window level, respectively, may permit more rapid adjustment of both the window width and window level, this input technique may present even more challenges in regards to adjusting the window width and window level in an accurate manner. Consequently, a user may have to repeatedly modify the window width and the window level in order to arrive at the desired settings, thereby undesirably consuming additional processing and imaging resources to adjust and then re-adjust the window width and window level in response to the repeated modifications.

BRIEF SUMMARY

A method, computing device and computer program product are provided in accordance with an example embodiment of the present invention in order to utilize a multitouch user interface so as to adjust the window width and window level of an image. By utilizing a multitouch user interface and by interpreting the user input in accordance with an example embodiment of the present invention, the window width and window level of an image may be adjusted in an intuitive manner and also in a manner that is both efficient and effective and that allows for accuracy in the adjustment of both the window width and window level of an image. Thus, a user may more readily review and interpret an image.

In an example embodiment, a method is provided that includes receiving an indication of user input provided via a multitouch user interface. The indication of user input includes an indication of respective positions of first and second fingers upon the multitouch user interface. The method of the example embodiment also includes adjusting, with processing circuitry, a window width of an image based upon a change in spacing between the first and second fingers. Further, the method of the example embodiment includes adjusting, with the processing circuitry, a window level of the image based upon a change in location of a reference point defined by the respective positions of the first and second fingers upon the multitouch user interface. For example, the reference point may be a mid-point between the respective positions of the first and second fingers upon the multitouch user interface.

The method of an example embodiment may adjust the window width in such a manner that the window width has a direct relationship to the change in spacing between the first and second fingers. The method of an example embodiment may adjust the window level based upon the change in location of the reference point along a line defined by the respective positions of the first and second fingers upon the multitouch user interface. For example, the method may adjust the window level based upon a direction along the line in which the location of the reference point is moved. In an example embodiment, the indication of the respective positions of the first and second fingers upon the multitouch user interface may include an indication of relative positions of the first and second fingers upon the multitouch user interface. In an example embodiment, the method may receive the indication of user input via a dedicated region of the multitouch user interface. Alternatively, the method may receive the indication of user input that is provided at a location overlying the image. In an example embodiment, the method may require a respective position of at least one of the first and second fingers to change by more than a predefined threshold prior to recognizing the change in position as the user input.

In another example embodiment, a computing device is provided that includes processing circuitry configured to receive an indication of the user input provided via a multitouch user interface. The indication of user input may include an indication of respective positions of the first and second fingers upon the multitouch user interface. The processing circuitry may also be configured to adjust a window width of the image based upon a change in spacing between the first and second fingers. The processing circuitry of this example embodiment may also be configured to adjust a window level of the image based upon a change in location of a reference point defined by the respective positions of the first and second fingers upon the multitouch user interface. For example, the reference point may be a mid-point between the respective positions of the first and second fingers upon the multitouch user interface.

The processing circuitry of an example embodiment may be configured to adjust the window level based upon the change in location of the reference point along the line defined by the respective positions of the first and second fingers upon the multitouch user interface. For example, the processing circuitry may be configured to adjust the window level based upon a direction along the line in which the location of the reference point is moved. The processing circuitry of an example embodiment may be configured to adjust the window width such that the window width has a direct relationship to the change in spacing between the first and second fingers. The processing circuitry may be configured to receive the indication of user input by receiving the indication of user input via the multitouch user interface of a Picture Archiving and Communication System (PACS) viewer so as to permit the window width and the window level of a medical image to be adjusted.

In a further embodiment, a computer program product is provided that includes at least one non-transitory computer-readable storage medium having computer-executable program code portions stored therein with the computer-executable program code portions including program code instructions for receiving an indication of user input provided via a multitouch user interface. Indication of the user input may include an indication of respective positions of first and second fingers upon the multitouch user interface. The computer-executable program code portions may also include program code instructions for adjusting a window width of an image based upon a change in spacing between the first and second fingers. The computer-executable program code portions may further include program code instructions for adjusting a window level of the image based upon a change in location of a reference point defined by the respective positions of the first and second fingers upon the multitouch user interface. The reference point may be, for example, a mid-point between the respective positions of the first and second fingers upon the multitouch user interface.

In an example embodiment, the program code instructions for adjusting the window width may be such that the window width has a direct relationship to the change in spacing between the first and second fingers. The program code instructions for adjusting the window level may include program code instructions for adjusting the window level based upon the change in location of the reference point along a line defined by the respective positions of the first and second fingers upon the multitouch user interface. For example, the program code instructions for adjusting the window level may include program code instructions for adjusting the window level based upon a direction along the line in which the location of the reference point is moved.

BRIEF DESCRIPTION OF THE DRAWINGS

Having thus described example embodiments of the present disclosure in general terms, reference will now be made to the accompanying drawings, which are not necessarily drawn to scale, and wherein:

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information" and similar terms may be used interchangeably to refer to data capable of being transmitted, received and/or stored in accordance with embodiments of the present invention. Thus, use of any such terms should not be taken to limit the spirit and scope of embodiments of the present invention.

Figure 1:
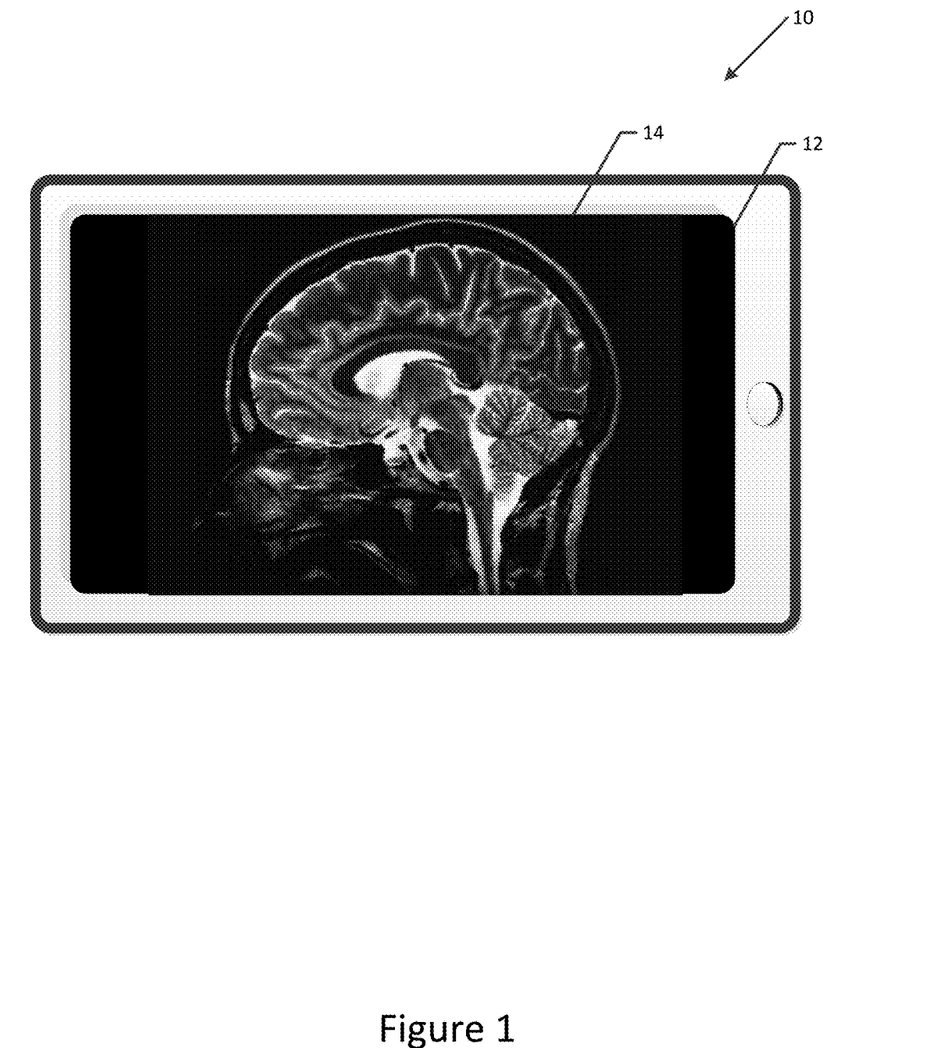
FIG. 1 depicts a tablet computer having a multitouch user interface that may be configured in accordance with an example embodiment of the present invention in order to permit the window level and the window width of the image presented upon the display to be adjusted.

A method, computing device and computer program product are provided in accordance with an example embodiment of the present invention in order to permit the window width and window level of an image to be adjusted by user input provided via a multitouch user interface. As described below, the multitouch user interface not only supports the mouse adjustment techniques, but also provides for new and more accurately represented techniques of adjustment. The user input may be provided via a wide variety of multitouch user interfaces. As shown in FIG. 1, for example, the multitouch user interface 12 may be embodied by a touchscreen, such as the touchscreen of a tablet computer 10 or other computing device, such as a mobile terminal, e.g., a laptop computer, a smartphone, a tablet or the like, a personal computer, a Picture Archiving and Communication System (PACS) viewer/workstation or the like. Regardless of the manner in which a touchscreen is embodied, the touchscreen may permit both the image 14 to be presented and user input to be provided via the touchscreen. Alternatively, the multitouch user interface may be separate from the display upon which the image is presented. For example, the image may be presented upon a display and a multitouch user interface in the form of a touch surface or the like may be provided to receive the user input and to control the window width and window level of the image presented by the display. Still further, the multitouch user interface may be configured in other manners while permitting the user input to be provided and interpreted in a manner that permits the controlled adjustment of both the window width and window level of an image.

As also shown in FIG. 1, the image 14 may be a medical image, such as an image of a patient. The image may have been captured by any of a wide variety of different modalities, such as CT, MRI, CR, DR, MG or the like. The image may be utilized for a wide variety of different purposes including diagnosis, treatment, training or the like. Still further, in an instance in which the image is an image of a portion of a patient, the image may be of any of a wide variety of different portions of the patient, such as a limb, organ or the like.

Figure 2:
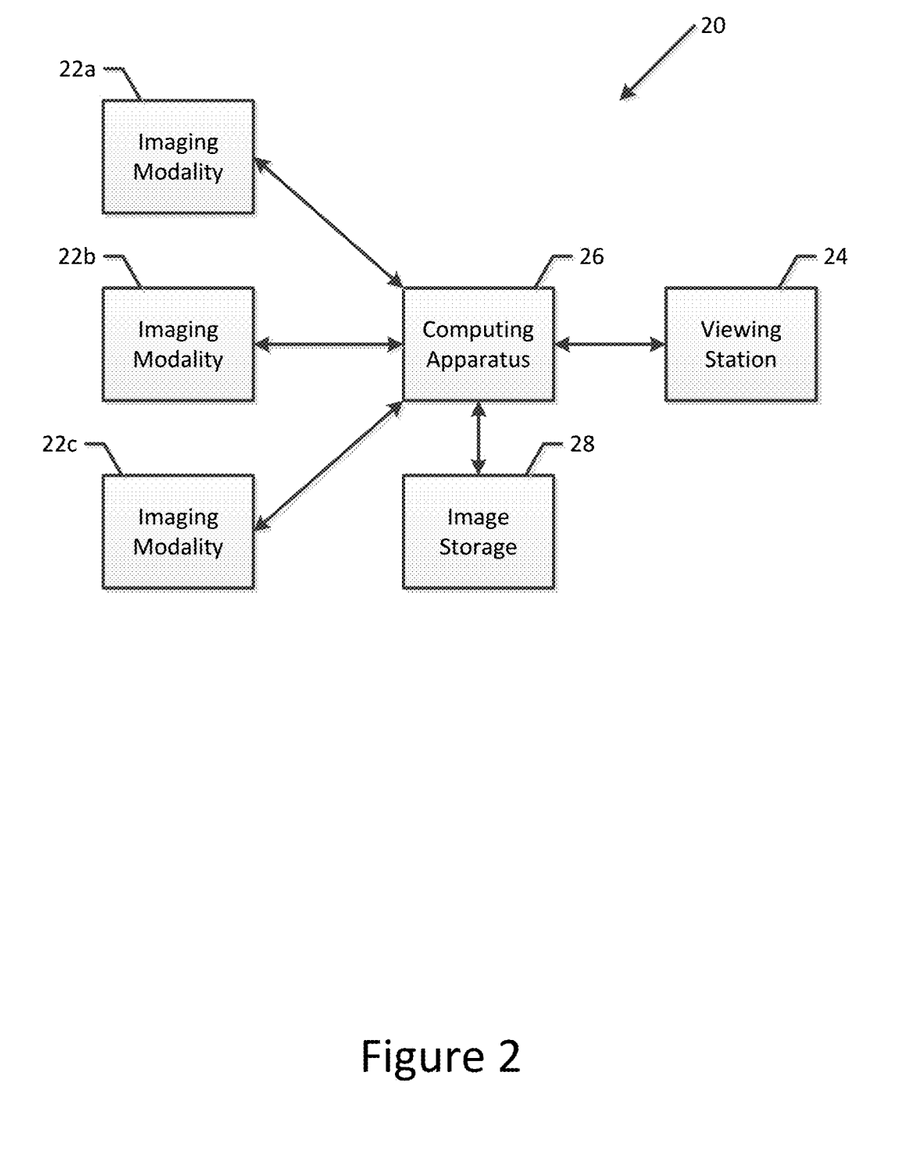
FIG. 2 is a block diagram of a system, such as a Picture Archiving and Communication System (PACS) that may be specifically configured in accordance with an example embodiment of the present invention.

By way of example, FIG. 2 illustrates a system 20 that may benefit from an example embodiment of the present invention. As shown, the system includes one or more imaging modalities (three example modalities being shown as modalities 22a, 22b and 22c) for acquiring an image, such as an image of the human body or parts of the human body for clinical purposes such as examination, diagnosis and/or treatment. Examples of suitable modalities include, for example, CT, MRI, CR, DR, MG or the like. The system also includes a viewing station 24 configured to receive an image from one or more modalities, and present the image such as for review by a medical professional such as a radiologist. In one example embodiment, the viewing station may be a PACS viewing station (or workstation) and may include the multitouch user interface 12. As also shown in FIG. 2, the PACS system may also include a computing apparatus 26 for receiving the images from the modalities and for providing the images to the viewing station. As described below, the computing apparatus may also be configured to process the images in some embodiments. Further, the PACS system may include image storage, such as a memory device for storing the images received from the modalities.

The imaging modalities 22, viewing station 24, computing apparatus 26 and/or image storage 28 may be configured to directly and/or indirectly communicate with one another in any of a number of different manners including, for example, any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G, 3G, 4G or Long Term Evolution (LTE) communication techniques, local area network (LAN), wireless LAN (WLAN) techniques or the like. In accordance with various ones of these techniques, the imaging modality, viewing station, computing apparatus and/or image storage can be coupled to and configured to communicate across one or more networks. The network(s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the imaging modality, viewing station and/or computing apparatus.

Regardless of the manner in which the multitouch user interface 12 is embodied, a computing device may be provided that is configured to receive the user input provided via the multitouch user interface and to provide for controlled adjustment of the window width and window level of the image 14 presented upon the display. For example, the computing device may include both the multitouch user interface and the display as well as the processing circuitry configured to interpret the user input and to provide for a controlled adjustment of the window width and window level. For example, the computing device may be embodied by a tablet computer 10, a laptop computer, a mobile terminal, e.g., a smartphone, a PACS viewer as described in conjunction with FIG. 2 or the like, or other computing device that includes both a multitouch user interface, a display and the processing circuitry for performing the various functions described hereinafter. Alternatively, the computing device may include the processing circuitry configured to receive the user input and to provide for controlled adjustment of the window width and window level of the image, but need not include the multitouch user interface and/or the display upon which the image is presented. In this example embodiment, the computing device may be in communication with the multitouch user interface and/or the display, such as via a wireless or wireline communication network. For example, the computing device may be a personal computer, a computer workstation, a server or other network-based computing device that interacts with the multitouch user interface and/or the display in order to perform certain functionalities, such as to controllably adjust the window width and the window level of an image. With reference to the embodiment of FIG. 2, for example, the computing device may be embodied by the computing apparatus 26 of the PACS system.

The multitouch user interface 12 may be embodied by any of a wide variety of user interfaces that are configured to receive and distinguish two or more touches at one time. As used herein, a touch may refer to a physical touch, such as the touch of a user's finger upon the surface of a user interface or the positioning of a user's finger in proximity to the user interface so as to be recognized as an input even though the user's finger does not physically contact the surface of the multitouch user interface. By way of example, a multitouch user interface may be configured to detect and recognize the different points of contact created by two fingers of the user upon the surface of the multitouch user interface. Based upon the movement of the fingers of the user upon the multitouch user interface as described below, the window width and window level of the image may be controllably adjusted.

Figure 3:
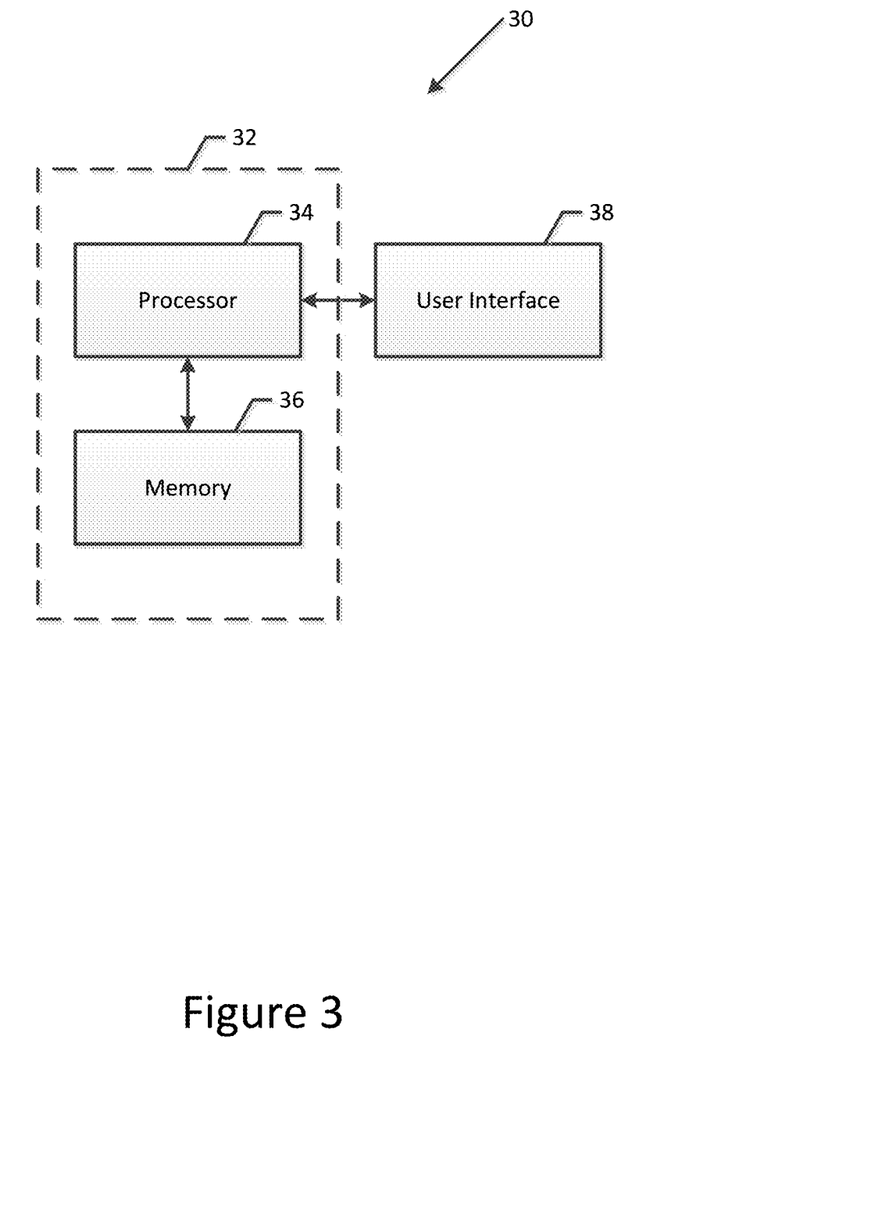
FIG. 3 is a block diagram of a computing device that may be specifically configured in accordance with an example embodiment of the present invention.

A computing device 30 in accordance with an example embodiment is depicted in FIG. 3. As shown, the computing device may include or be associated and in communication with processing circuitry 32 that is configurable to perform functions in accordance with one or more example embodiments disclosed herein. In this regard, the processing circuitry may be configured to perform and/or control performance of one or more functionalities of the computing device in accordance with various example embodiments, and thus may provide means for performing functionalities of the computing device. The processing circuitry may be configured to perform data processing, application execution and/or other processing and management services according to one or more example embodiments.

In some example embodiments, the processing circuitry 32 may include a processor 34 and, in some embodiments, such as that illustrated in FIG. 3, may further include memory 36. The processing circuitry may be in communication with or otherwise control a user interface 38, such as a display, a touchscreen, a touch surface, a keyboard and/or other input/output mechanisms and, in some embodiments, may also optionally include a communication interface for communicating with other computing systems. As such, the processing circuitry may be embodied as a circuit chip (e.g., an integrated circuit chip) configured (e.g., with hardware, software or a combination of hardware and software) to perform operations described herein.

The processor 34 may be embodied in a number of different ways. For example, the processor may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. Although illustrated as a single processor, it will be appreciated that the processor may comprise a plurality of processors. The plurality of processors may be in operative communication with each other and may be collectively configured to perform one or more functionalities of the computing device as described herein. The plurality of processors may be embodied on a single computing device or distributed across a plurality of computing devices collectively configured to function as the computing device. In some example embodiments, the processor may be configured to execute instructions stored in the memory 36 or otherwise accessible to the processor. As such, whether configured by hardware or by a combination of hardware and software, the processor may represent an entity (e.g., physically embodied in circuitry—in the form of processing circuitry 32) capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions may specifically configure the processor to perform one or more operations described herein.

The processing circuitry 32 may also include memory 36 as shown in FIG. 3. In some example embodiments, the memory may include one or more non-transitory memory devices such as, for example, volatile and/or non-volatile memory that may be either fixed or removable. In this regard, the memory may comprise a non-transitory computer-readable storage medium. It will be appreciated that while the memory is illustrated as a single memory, the memory may comprise a plurality of memories. The plurality of memories may be embodied on a single computing device or may be distributed across a plurality of computing devices collectively configured to function as the computing device. The memory may be configured to store information, data, applications, instructions and/or the like for enabling the computing device to carry out various functions in accordance with one or more example embodiments. For example, the memory may be configured to buffer input data for processing by the processor 34. Additionally or alternatively, the memory may be configured to store instructions for execution by the processor. As yet another alternative, the memory may include one or more databases that may store a variety of files, contents or data sets, such as medical images, e.g., image studies, for a plurality of patients. Among the contents of the memory, applications may be stored for execution by the processor in order to carry out the functionality associated with each respective application. In some cases, the memory may be in communication with one or more of the processor or the user interface 38 via a bus or buses for passing information among components of the computing device.

In addition to the processing circuitry 32, the computing device 30 may include a user interface 38 for displaying and/or receiving data, content or the like. The user interface may include one or more earphones and/or speakers, a display, and/or a user input interface, such as the multitouch user interface 12. The user interface, in turn, can include any of a number of devices allowing the computing device to receive data from a user, such as a microphone, a keypad, a touch-sensitive surface (integral or separate from the monitor), a joystick, or other input device. As will be appreciated, the processing circuitry may be directly connected to other components of the computing device, or may be connected via suitable hardware. In one example, the processing circuitry may be connected to the user interface via an adapter configured to permit the processing circuitry to send graphical information to the user interface.

Having now described a computing device 30 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Figure 4:
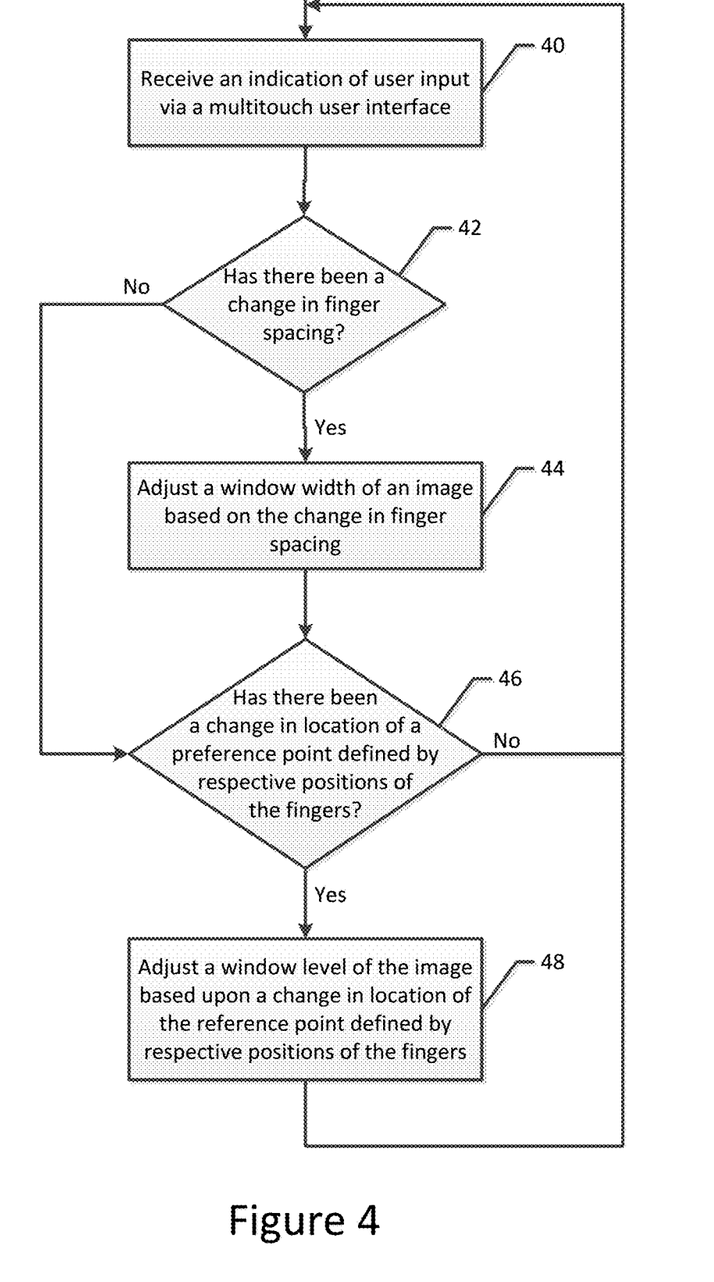
FIG. 4 is a flowchart illustrating the operations performed, such as by the computing device of FIG. 3, in accordance with an example embodiment of the present invention.

Referring now to FIG. 4, the operations performed, such as by the computing device 30 of FIG. 3, in order to receive user input via a multitouch user interface 12 and to provide for controlled adjustment of the window width and the window level of an image 14 are illustrated in accordance with an example embodiment of the present invention. As shown in block 40, the computing device may include means, such as the user interface 38, the processing circuitry 32, the processor 34 or the like, for receiving an indication of user input provided via the multitouch user interface. The indication of the user input may include an indication of the respective positions of at least first and second fingers of the user upon the multitouch user interface. In this regard, the indication of the respective position of the first and second fingers of the user may define the absolute position of the first and second fingers of the user upon the multitouch user interface or the relative position of the first and second fingers upon the multitouch user interface, such as the position of the first and second fingers upon the multitouch user interface relative to one another. As referenced herein, the respective positions of the first and second fingers upon the multitouch user interface generally refer to the respective points of contact established by the first and second fingers on the surface of the multitouch user interface, either by direct contact or based upon the first and second fingers being proximate to the multitouch user interface so that the positions of the fingers may be identified and tracked, such as by a capacitive proximity sensor.

Based upon the respective positions of the first and second fingers upon the multitouch user interface 12, the computing device 30, such as the processing circuitry 32, the processor 34 or the like, may be configured to determine the initial spacing between the first and second fingers. Additionally, the computing device, such as the processing circuitry, the processor or the like, may be configured in some embodiments to also determine a line defined between the initial positions of the first and second fingers upon the multitouch user interface.

Figure 5:
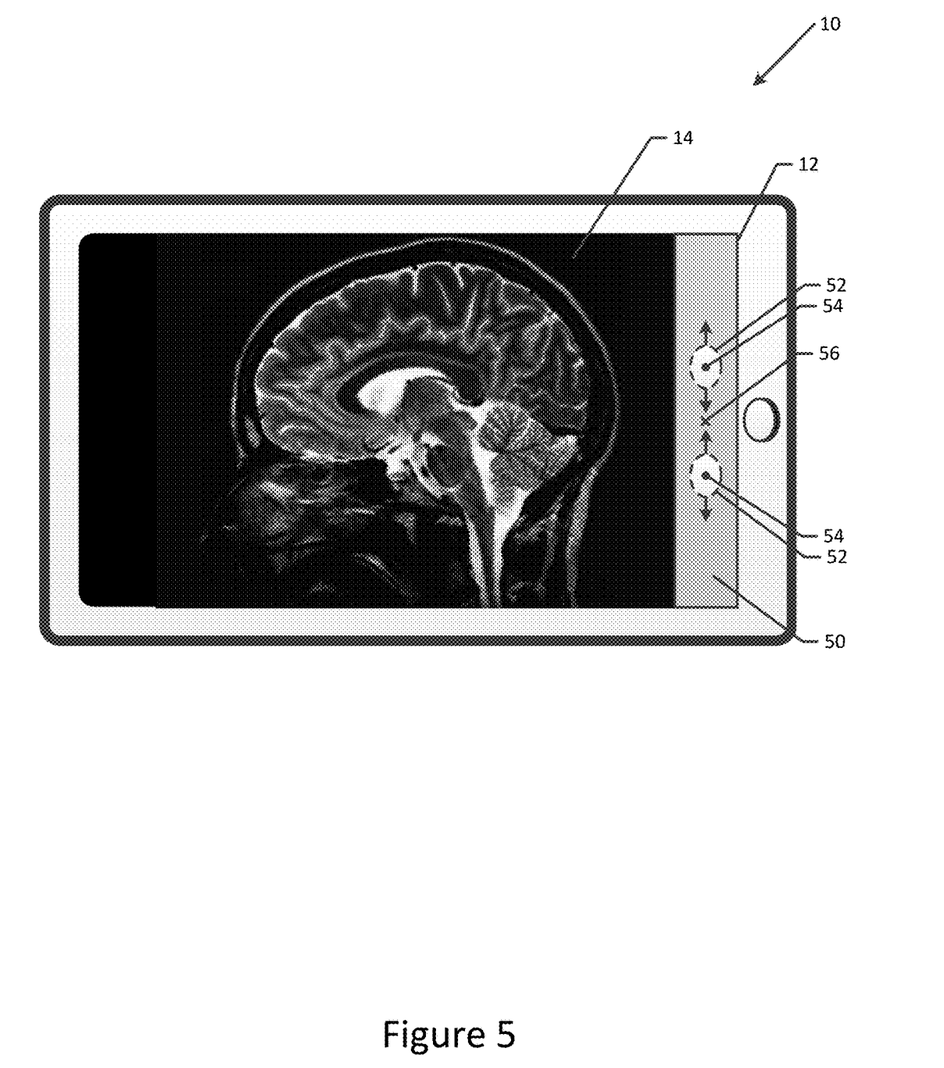
FIG. 5 depicts a multitouch user interface, such as of a tablet computer, having a dedicated area in which to receive user input for adjusting the window width and/or window level of the image in accordance with an example embodiment of the present invention.
Figure 6:
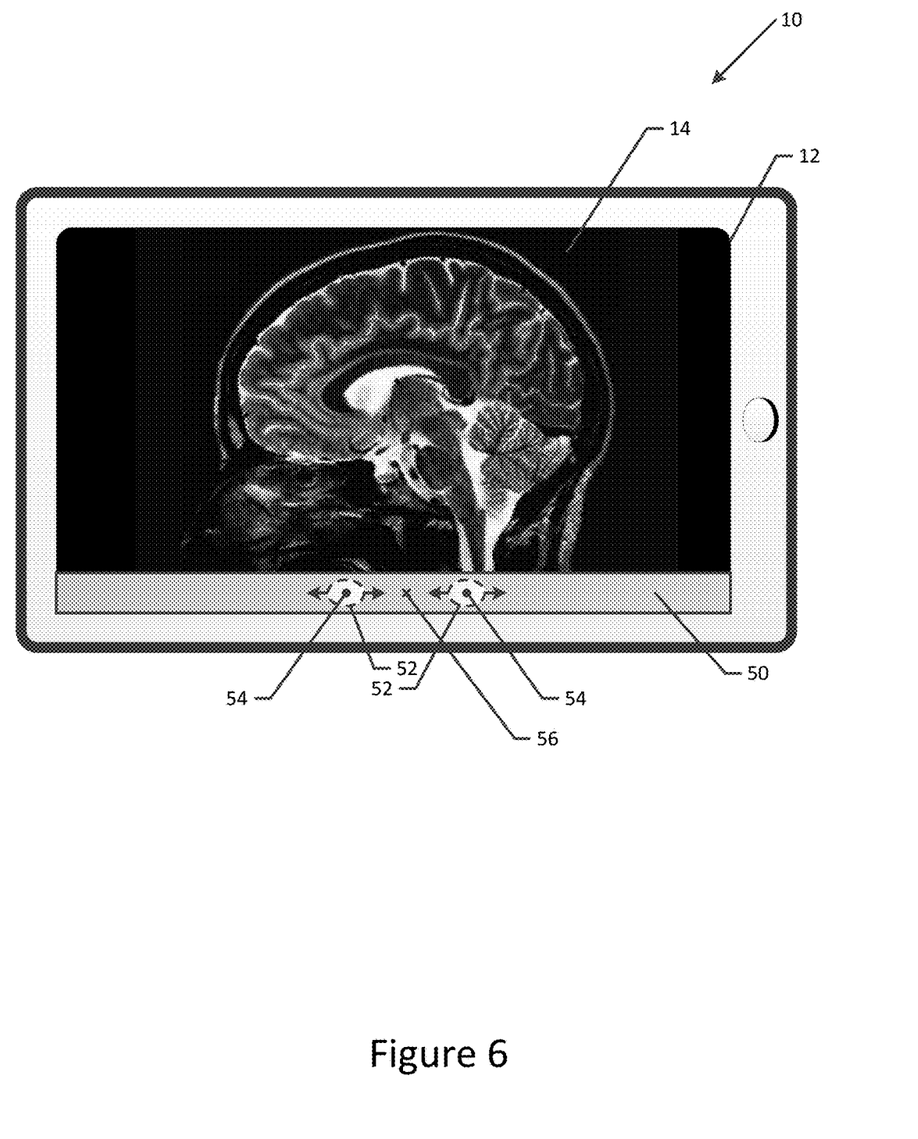
FIG. 6 depicts a multitouch user interface, such as of a tablet computer, having a dedicated area in which to receive user input for adjusting the window width and/or window level of the image in accordance with an example embodiment of the present invention.
Figure 7:
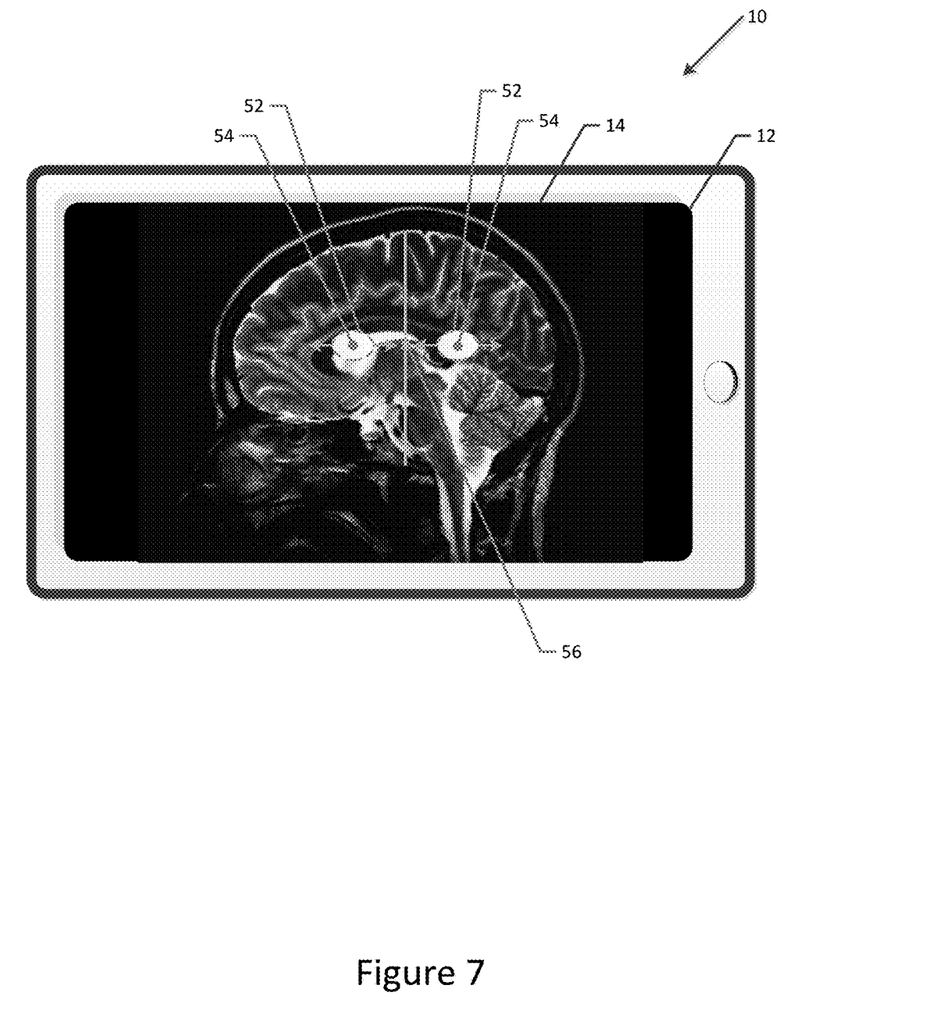
FIG. 7 depicts a multitouch user interface that is configured to receive user input for adjusting the window width and/or window level that is provided at a location overlying the image in accordance with an example embodiment of the present invention.

Although the user input may be provided via a multitouch user interface 12 that is separate from the display that is configured to present the image 14, the multitouch user interface may be configured to both present the image and to receive the user input, such as in an instance in which the multitouch user interface is embodied by a touchscreen, such as shown in FIG. 1. In this example embodiment, the multitouch user interface may be configured to include a region within which the image is displayed and another dedicated region via which the user input is provided. As shown in FIGS. 5 and 6, for example, the multitouch user interface may include a dedicated region 50 to receive the user input. The dedicated region may be of various shapes and sizes and may be positioned relative to the image in various manners. In this regard, the dedicated region for receiving user input may be defined in various manners both relative to the multitouch user interface and relative to the region of the multitouch user interface within which the image is presented. As shown in FIG. 5, for example, the dedicated region for receiving the user input may extend vertically alongside the image, e.g., either to the right of the image as illustrated or to the left of the image. Alternatively, as shown in FIG. 6, the dedicated region for receiving the user input may extend horizontally alongside the image, e.g., either below the image as illustrated or above the image. In contrast to the embodiments of the multitouch user interface that include a dedicated region for receiving the user input, the multitouch user interface of another embodiment may be configured so that the user input is provided, not within a dedicated region separate from the region in which the image is displayed, but at a location that overlies the image presented by the multitouch user interface, such as shown in FIG. 7.

A computing device 30 may also include means, such as the processing circuitry 32, the processor 34 or the like, for determining whether there has been a change in spacing between the first and second fingers and, if so, then adjusting the window width of an image based upon the change in spacing between the first and second fingers upon the multitouch user interface 12. See blocks 42 and 44 of FIG. 4. As shown in FIGS. 5-7, the first and second fingers may contact the multitouch user interface at first and second regions 52 and the processing circuitry may define the spacing between the first and second fingers to be the linear spacing between the center points 54 of the regions at which the first and second fingers contact the multitouch user interface. For example, the processing circuitry may be configured to adjust the window width of an image based upon movement of one or both of the first and second fingers away from the other as represented by the outwardly directed arrows of FIGS. 5-7 so as to increase the spacing therebetween. Similarly, the processing circuitry may be configured to adjust the window width of an image in response to movement of one or both of the first and second fingers toward the other as represented by the inwardly directed arrows of FIGS. 5-7 in order to reduce the spacing therebetween. Thus, the user input provided by the first and second fingers upon the multitouch user interface may be changed by spreading the first and second fingers further from each other or by pinching the first and second fingers toward one another.

In an example embodiment, the processing circuitry 32 may be configured to adjust the window width such that the window width has a direct relationship to the change in spacing between the first and second fingers. Thus, as the spacing between the first and second fingers is increased, such as in response to the spreading of the first and second fingers further apart from one another, the window width may be correspondingly increased. By increasing the window width, a larger range of image pixel values are displayed between the maximum and minimum values of the display such that the differences between the pixels is less noticeable, thereby decreasing the contrast. Conversely, in an instance in which the spacing between the first and second fingers is reduced, such as by pinching the first and second fingers towards one another, the window width may be correspondingly reduced. By reducing the window width, a smaller range of image pixel values are displayed between the maximum and minimum values of the display such that the differences between the pixels is more noticeable, thereby increasing the contrast. In an example embodiment, the extent to which the window width is adjusted, such as by being either increased or decreased, may be proportional to the change in spacing between the first and second fingers. However, the window width may be adjusted in other manners in response to a change in spacing between the first and second fingers in other embodiments.

The computing device 30 may also include means, such as the processing circuitry 32, the processor 34 or the like, for determining whether there has been a change in location of a reference point defined by the respective positions of the first and second fingers upon the multitouch user interface 12 and, if so, then adjusting the window level of the image based upon the change in location of the reference point. See blocks 46 and 48 of FIG. 4. The change in the window level of the image may cause the brightness of the image to be correspondingly modified. The reference point may be defined by the respective positions of the first and second fingers in various manners. For example, the reference point may be defined to be the mid-point 56 between the respective positions of the first and second fingers upon the multitouch user interface, such as the mid-point between the center points 54 of the regions 52 at which the first and second fingers contact the multitouch user interface. In this example embodiment, spreading or pinching of the first and second fingers in a motion in which the first and second fingers move by equal distances will not change the reference point and, as a result, will not cause the window level to be adjusted since the mid-point between the respective positions of the first and second fingers will remain the same. However, movement of the first and second fingers by different distances or movement of the first and second fingers in the same direction, such as by sliding both the first and second fingers to the right or to the left, will cause the mid-point between the respective positions of the first and second fingers to change which, in turn, will cause the window level of the image to be adjusted accordingly.

In an example embodiment, the reference point may be defined along a line defined by the respective positions of the first and second fingers upon the multitouch user interface 12. For example, a line may be defined by the computing device 30, such as the processing circuitry 32, the processor 34 or the like, that extends between the positions at which the first and second fingers contact the multitouch user interface. The reference point may, in turn, be defined to be a mid-point 56 of the line between the first and second fingers. In this example embodiment, the processing circuitry may be configured to adjust the window level based upon the change in location of the reference point along the line defined by the respective positions of the first and second fingers. For example, the processing circuitry may be configured to adjust the window level based upon the direction along the line in which the location of the reference point is moved. In this regard, the processing circuitry may be configured to increase the window level in response to movement of the reference point in a first direction along the line and to decrease the window level in response to movement of the reference point in a second direction, opposite the first direction, along the line.

By way of example, in an instance in which the first and second fingers are positioned so as to define a horizontal line therebetween, in response to movement of the first and second fingers to the right which, in turn, causes the reference point, e.g., the mid-point 56, to be correspondingly moved to the right along the line, the processing circuitry 32 may be configured to increase the window level of the image, thereby increasing the brightness of the image. Conversely, in response to movement of the first and second fingers to the left which, in turn, causes the reference point, e.g., the mid-point, to be correspondingly moved to the left along the line, the processing circuitry may be configured to decrease the window level of the image, thereby decreasing the brightness of the image. By way of another example, in an instance in which the first and second fingers are positioned so as to define a vertical line therebetween, in response to upward movement of the first and second fingers that causes the reference point, e.g., the mid-point, to be correspondingly moved upwardly along the line, the processing circuitry may be configured to increase the window level of the image. Conversely, in response to downward movement of the first and second fingers which, in turn, causes the reference point, e.g., the mid-point, to be correspondingly moved downwardly along the line, the processing circuitry may be configured to decrease the window level of the image.

The processing circuitry 32 may be configured to adjust the window level of the image to an extent that is based upon the magnitude of the change in location of the reference point with larger adjustments in the window level of the image being occasioned by larger changes in location of the reference point and smaller adjustments in the window level of the image being occasioned by smaller changes in the location of the reference point. In an example embodiment, the extent to which the window level is adjusted, such as by being either increased or decreased, may be proportional to the change in the location of the reference point.

The computing device 30, such as the processing circuitry 32, the processor 34 or the like, may be configured to independently adjust the window width and window level of the image in response to the user input. For example, the window width of an image may be adjusted without correspondingly adjusting the window level of the image by changing the spacing between the first and second fingers in a manner that does not alter the reference point defined by the respective positions of the first and second fingers. In this regard, spreading or pinching the first and second fingers such that the first and second fingers move the same distance outward in a spreading gesture or inward in a pinching gesture does not change the mid-point 56 between the fingers. Similarly, the window level of the image may be adjusted independent of any adjustment of the window width of the image. For example, the first and second fingers may be moved upon the multitouch user interface 12 such that the reference point defined by the respective position of the first and second fingers is changed without altering the spacing between the first and second fingers, such as by sliding the first and second fingers in a common direction without altering the spacing therebetween. However, user input may be provided in other instances so as to cause both the window width and window level of an image to be adjusted in response to the same movement of the first and second fingers. For example, a user may concurrently slide the first and second fingers in the same direction along the multitouch user interface while changing the spacing between the first and second fingers such that the processing circuitry will cause both the window width and window level of the image to be concurrently adjusted.

The computing device 30, such as the processing circuitry 32, the processor 34 or the like, may be configured to associate the physical input movement to the bit depth of the image under control to provide an improved sense of control over the image and to reduce instances in which the image must be repeatedly modified in an effort to properly represent the image. In this regard, mouse interfaces for window leveling adjustment do not generally adapt the extent of the input movement to the image under control. For example, with respect to an image in which the pixels are each represented by 10 bits, a small movement of the mouse may send the image window width or level beyond the intended input and require further user input (in the opposite direction) to correct the representation of the image. As another example, with respect to a 14 bit image, an undesirably large movement of the mouse may be required to cause the widow width or level to change much at all. Thus, the computing device, such as the processing circuitry, the processor or the like, may be configured to modify the physical input movement that is required to alter the window width and/or level to the bit depth of the image under control, thereby permitting the image to be more readily controlled in the desired manner.

The method, computing device 30 and computer program product of an example embodiment permit both the window level and window width to be adjust in an intuitive and a precise manner. In this regard, the user input performed by movement of the first and second fingers may map more closely to and more intuitively with the window leveling pixel operations of the image, such as presented by a PACS system. As such, the processing and imaging resources consumed by the adjustments to the window level and the window width may be conserved by permitting the window level and the window width to be precisely adjusted so as to reduce instances in which the window level and/or the window width must be repeatedly readjusted in order to arrive at the desired settings.

The type of change to the window level, such as an increase or a decrease, associated with movement in each of the opposed directions along the line defined between the initial positions of the first and second fingers may be predefined and/or may be configurable by a user. Similarly, the type of change to the window width, such as an increase or a decrease, associated with increases or decreases between the first and second fingers may be predefined and/or may be configurable by a user.

In an example embodiment, the computing device 30, such as the processing circuitry 32, the processor 34 or the like, may be configured so as to require the respective positions of the first and second fingers to change by more than a predefined threshold prior to recognizing the change in position as user input. As such, the computing device of this example embodiment may include means, such as the processing circuitry, the processor or the like, for requiring a respective position of at least one of the first or second fingers to change by more than a predefined threshold prior to recognizing the change in position as the user input, thereby reducing jitter. In this regard, the predefined threshold may be defined in terms of a predefined distance, thereby requiring the position of a finger to change by more than the predefined distance prior to recognizing the change in position as user input. Thus, in this example embodiment, a change in position of less than the predefined distance will not be recognized as user input, while a change in position that is greater than the predefined distance will be recognized as user input. The predefined threshold may be defined in other manners. For example, in another embodiment, the predefined threshold may be defined in terms of a predefined percentage, thereby requiring the position of a finger to change by more than the predefined percentage of the initial distance between the first and second fingers prior to recognizing the change in position as user input. As such, the computing device of this example embodiment may require a meaningful change in position to recognize the change in position as user input and will not respond to minor changes in position that do not satisfy the predefined threshold, thereby avoiding repeated adjustments to the window width and window level brought about by small, potentially inadvertent, positional changes of the first and second fingers upon the multitouch user interface 12.

The computing device 30 of an example embodiment, such as the processing circuitry 32, the processor 34, the user interface 38 or the like, may be configured to support clutching in which the first and second fingers are lifted from one region of the multitouch user interface 12 and are placed back in contact with a different region of the multitouch user interface. For example, the first and second fingers may be lifted from the multitouch user interface in an instance in which further movement of the fingers would be limited by the edge of the multitouch user interface. In this example embodiment, the return of the first and second fingers in contact with a different region of the multitouch user interface, such as within a predefined period of time from lifting the fingers from multitouch user interface, may be treated by the processing circuitry as a continuation of the same user input that was begun prior to having lifted the first and second fingers from the multitouch user interface. In this embodiment, the processing circuitry may be configured to again define the line between the first and second fingers once the fingers have been placed back in contact with the multitouch user interface as the line defined between the first and second fingers may have changed as a result of the clutching. Further, in an instance in which the multitouch user interface defines a dedicated region in which to receive the user input regarding window width and window level adjustments, such as shown in FIGS. 5 and 6, the processing circuitry and/or the user interface may be configured to only recognize the return of the first and second fingers to the multitouch user interface in an instance in which the first and second fingers are placed back into contact with the dedicated region of the multitouch user interface.

As described above, FIG. 4 is a flowchart of a method, computing device 30 and computer program product according to example embodiments of the invention. It will be understood that each block of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices 36 of a computing device and executed by processing circuitry 32 in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture which implements the function specified in the flowchart block(s). The computer program instructions of one or more computer program products may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks or steps of the flowchart support combinations of means for performing the specified functions and combinations of steps for performing the specified functions. It will also be understood that one or more blocks of the flowchart, and combinations of blocks in the flowchart, may be implemented by special purpose hardware-based computer systems which perform the specified functions or steps, or combinations of special purpose hardware and computer program product(s).

The above described functions may be carried out in many ways. For example, any suitable means for carrying out each of the functions described above may be employed to carry out embodiments of the invention. In one embodiment, a suitably configured processing circuitry 22 may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A method comprising:
receiving a user input provided via a multitouch user interface, wherein the user input comprises an indication of respective positions of first and second fingers upon the multitouch user interface;
adjusting, with processing circuitry, a window width of an image for controlling contrast of the image based upon a change in spacing between the first and second fingers of the user input upon the multitouch user interface;
adjusting, with the processing circuitry, a window level of the image for controlling brightness of the image based upon a change in location of a reference point, wherein the reference point is defined along a line defined by the respective positions of the first and second fingers of the user input upon the multitouch user interface,
wherein the reference point is changed by movement of the first and second fingers by different distances from the reference point or by sliding both of the first and second fingers in the same direction, and as a result of the change in location of the reference point, the window level of the image is alternatively increased or decreased depending upon a direction along the line in which the location of the reference point moved,
wherein the reference point is not changed by movement of the first and second fingers by equal distances from the reference point, and as a result, the reference point between the respective positions of the first and second fingers of the user input remains the same and the window level of the image is not changed, and
adjusting, with the processing circuitry, both the window width and the window level of the image based upon the user input in which both the spacing between the first and second fingers of the user input is changed while concurrently changing the location of the reference point by movement of the first and second fingers by different distances from the reference point or by sliding both of the first and second fingers in the same direction such that both the window width and the window level of the image are adjusted in response to a same movement of the first and second fingers of the user input upon the multitouch user interface.

2. A method according to claim 1 wherein the reference point is a midpoint between the respective positions of the first and second fingers of the user input upon the multitouch user interface.

3. A method according to claim 1 wherein adjusting the window width of the image comprises adjusting the window width such that the window width of the image has a direct relationship to the change in spacing between the first and second fingers of the user input upon the multitouch user interface.

4. A method according to claim 1 wherein receiving the indication of user input comprises receiving the indication of user input provided via a dedicated region of the multitouch user interface, wherein the dedicated region can be positioned vertically alongside the image, either at the right or left of the image, or the dedicated region can be positioned horizontally alongside the image, either below or above of the image.

5. A method according to claim 1 wherein receiving the indication of user input comprises receiving the indication of user input provided at a location overlying the image presented on the multitouch user interface.

6. A method according to claim 1 wherein receiving the indication of user input comprises requiring a respective position of at least one of the first or second fingers of the user input to change by more than a predefined threshold prior to recognizing the change in position as the user input.

7. A method according to claim 1 wherein receiving an indication of user input comprises:
detecting that the first and second fingers of the user input that have been removed from the multitouch user interface are returned into contact with the multitouch user interface within a predefined period of time following removal of the first and second fingers of the user input from the multitouch user interface; and
treating the first and second fingers of the user input that have returned into contact with the multitouch user interface as a continuation of the user input that was begun prior to the removal of the first and second fingers of the user input from the multitouch user interface.

8. A computing device comprising processing circuitry having a processor, wherein the processing circuitry is configured to:
receive a user input provided via a multitouch user interface, wherein the user input comprises an indication of respective positions of first and second fingers upon the multitouch user interface;
adjust a window width of an image for controlling contrast of the image based upon a change in spacing between the first and second fingers of the user input upon the multitouch user interface;
adjust a window level of the image for controlling brightness of the image based upon a change in location of a reference point, wherein the reference point is defined along a line defined by the respective positions of the first and second fingers of the user input upon the multitouch user interface,
wherein the reference point is changed by movement of the first and second fingers by different distances from the reference point or by sliding both of the first and second fingers in the same direction, and as a result of the change in location of the reference point, the window level of the image is alternatively increased or decreased depending upon a direction along the line in which the location of the reference point moved,
wherein the reference point is not changed by movement of the first and second fingers by equal distances from the reference point, and as a result, the reference point between the respective positions of the first and second fingers of the user input remains the same and the window level of the image is not changed, and
adjust both the window width and the window level of the image based upon the user input in which both the spacing between the first and second fingers of the user input is changed while concurrently changing the location of the reference point by movement of the first and second fingers by different distances from the reference point or by sliding both of the first and second fingers in the same direction such that both the window width and the window level of the image are adjusted in response to a same movement of the first and second fingers of the user input upon the multitouch user interface.

9. A computing device according to claim 8 wherein the reference point is a mid-point between the respective positions of the first and second fingers of the user input upon the multitouch user interface.

10. A computing device according to claim 8 wherein the processing circuitry is configured to adjust the window width of the image by adjusting the window width such that the window width of the image has a direct relationship to the change in spacing between the first and second fingers of the user input upon the multitouch user interface.

11. A computing device according to claim 8 wherein the processing circuitry is configured to receive the indication of user input by receiving the indication of user input via the multitouch user interface of a Picture Archiving and Communication System (PACS) viewer, and wherein the processing circuitry is configured to adjust the window width and the window level of a medical image.

12. A computing device according to claim 8 wherein the processing circuitry is configured to receive an indication of user input by:
detecting that the first and second fingers of the user input that have been removed from the multitouch user interface are returned into contact with the multitouch user interface within a predefined period of time following removal of the first and second fingers of the user input from the multitouch user interface; and
treating the first and second fingers of the user input that have returned into contact with the multitouch user interface as a continuation of the user input that was begun prior to the removal of the first and second fingers of the user input from the multitouch user interface.

13. A computer program product comprising a non-transitory computer-readable storage medium having computer-executable program code portions stored therein, the computer-executable program code portions comprising program code instructions for:
receiving a user input provided via a multitouch user interface, wherein the user input comprises an indication of respective positions of first and second fingers upon the multitouch user interface;
adjusting a window width of an image for controlling contrast of the image based upon a change in spacing between the first and second fingers of the user input upon the multitouch user interface;
adjusting a window level of the image for controlling brightness of the image based upon a change in location of a reference point, wherein the reference point is defined along a line defined by the respective positions of the first and second fingers of the user input upon the multitouch user interface,
wherein the reference point is changed by movement of the first and second fingers by different distances from the reference point or by sliding both of the first and second fingers in the same direction, and as a result of the change in location of the reference point, the window level of the image is alternatively increased or decreased depending upon a direction along the line in which the location of the reference point moved,
wherein the reference point is not changed by movement of the first and second fingers by equal distances from the reference point, and as a result, the reference point between the respective positions of the first and second fingers of the user input remains the same and the window level of the image is not changed, and
adjusting both the window width and the window level of the image based upon the user input in which both the spacing between the first and second fingers of the user input is changed while concurrently changing the location of the reference point by movement of the first and second fingers by different distances from the reference point or by sliding both of the first and second fingers in the same direction such that both the window width and the window level of the image are adjusted in response to a same movement of the first and second fingers of the user input upon the multitouch user interface.

14. A computer program product according to claim 13 wherein the reference point is a mid-point between the respective positions of the first and second fingers of the user input upon the multitouch user interface.

15. A computer program product according to claim 13 wherein the program code instructions for adjusting the window width of the image comprise program code instructions for adjusting the window width such that the window width of the image has a direct relationship to the change in spacing between the first and second fingers of the user input upon the multitouch user interface.

16. A computer program product according to claim 13 wherein the program code instructions for receiving an indication of user input comprise program code instructions for:
  detecting that the first and second fingers of the user input that have been removed from the multitouch user interface are returned into contact with the multitouch user interface within a predefined period of time following removal of the first and second fingers of the user input from the multitouch user interface; and
  treating the first and second fingers of the user input that have returned into contact with the multitouch user interface as a continuation of the user input that was begun prior to the removal of the first and second fingers of the user input from the multitouch user interface.

* * * * *